United States Patent
Field et al.

(10) Patent No.: US 8,753,305 B2
(45) Date of Patent: Jun. 17, 2014

(54) BUBBLE-DRIVEN IOP CONTROL SYSTEM

(75) Inventors: Leslie Field, Portola Valley, CA (US); Matthew Rickard, Yorba Linda, CA (US)

(73) Assignee: Alcon Research, Ltd., Fort Worth, TX (US)

( * ) Notice: Subject to any disclaimer, the term of this patent is extended or adjusted under 35 U.S.C. 154(b) by 64 days.

(21) Appl. No.: 13/311,727

(22) Filed: Dec. 6, 2011

(65) Prior Publication Data

US 2013/0144202 A1    Jun. 6, 2013

(51) Int. Cl.
*A61M 5/00*    (2006.01)

(52) U.S. Cl.
USPC .......................................................... 604/9

(58) Field of Classification Search
USPC ............... 604/7–9, 20–21, 65–67, 294, 298; 606/6
See application file for complete search history.

(56) References Cited

U.S. PATENT DOCUMENTS

| | | | |
|---|---|---|---|
| 4,089,329 A | 5/1978 | Couvillon et al. | |
| 4,206,762 A | 6/1980 | Cosman | |
| 4,457,757 A | 7/1984 | Molteno | |
| 4,656,827 A | 4/1987 | Puillet | |
| 4,750,901 A | 6/1988 | Molteno | |
| 4,922,913 A | 5/1990 | Waters et al. | |
| 4,938,742 A * | 7/1990 | Smits ............................. | 604/67 |
| 5,005,577 A | 4/1991 | Frenkel | |
| 5,178,604 A | 1/1993 | Baerveldt | |
| 5,179,953 A | 1/1993 | Kursar | |
| 5,397,300 A | 3/1995 | Baerveldt | |
| 5,476,445 A | 12/1995 | Baerveldt | |
| 5,558,629 A | 9/1996 | Baerveldt | |
| 5,891,097 A * | 4/1999 | Saito et al. ..................... | 604/141 |
| 6,007,511 A | 12/1999 | Prywes | |
| 6,048,328 A * | 4/2000 | Haller et al. ............. | 604/288.03 |
| 6,447,449 B1 | 9/2002 | Fleischman et al. | |
| 6,579,235 B1 | 6/2003 | Abita et al. | |
| 6,589,198 B1 | 7/2003 | Soltanpour et al. | |
| 6,682,500 B2 | 1/2004 | Soltanpour et al. | |
| 6,712,764 B2 | 3/2004 | Jeffries et al. | |

(Continued)

FOREIGN PATENT DOCUMENTS

| | | |
|---|---|---|
| WO | WO 93/03665 | 3/1993 |
| WO | WO 98/03665 | 1/1998 |

(Continued)

OTHER PUBLICATIONS

Byunghoon Bae, Hongseok Kee, Seonho Kim, Yeon Lee, Taeseok Sim, Yongkweon Him and Kyihwan Park; "In Vitro Experiment of the Pressure Regulating Valve for a Glaucoma Impact"; Journal of Micromechanics and Microengineering, 13 (2003); pp. 613-619.

(Continued)

*Primary Examiner* — Tan-Uyen T Ho
*Assistant Examiner* — Mark K Han
(74) *Attorney, Agent, or Firm* — Haynes and Boone, LLP

(57) ABSTRACT

An intraocular pressure control system for implantation in an eye of a patient to provide drainage from an anterior chamber of the eye to a drainage location at the eye includes a drainage tube and a valve system arranged to control drainage flow between the anterior chamber and the drainage site, the valve system being configured to control fluid flow using an electrolysis process and closed loop feedback from pressure sensors able to determine: flow rate, IOP, bleb pressure, and internal valve pressure.

28 Claims, 4 Drawing Sheets

(56) References Cited

U.S. PATENT DOCUMENTS

| | | | |
|---|---|---|---|
| 6,749,568 B2 | 6/2004 | Fleischman et al. | |
| 6,939,299 B1 | 9/2005 | Petersen et al. | |
| 7,137,952 B2 | 11/2006 | Leonardi et al. | |
| 7,169,106 B2 | 1/2007 | Fleischman et al. | |
| 7,252,006 B2 | 8/2007 | Tai et al. | |
| 7,354,416 B2 | 4/2008 | Quiroz-Mercado et al. | |
| 7,409,863 B2 | 8/2008 | Bateman et al. | |
| 7,612,328 B2 | 11/2009 | Kaiser | |
| 7,887,508 B2 * | 2/2011 | Meng et al. | 604/114 |
| 8,419,673 B2 * | 4/2013 | Rickard | 604/9 |
| 2001/0000527 A1 | 4/2001 | Yaron et al. | |
| 2002/0049374 A1 | 4/2002 | Abrea | |
| 2002/0099359 A1 | 7/2002 | Santini, Jr. et al. | |
| 2002/0143284 A1 | 10/2002 | Tu et al. | |
| 2002/0193674 A1 | 12/2002 | Fleischman et al. | |
| 2003/0078487 A1 | 4/2003 | Jeffries et al. | |
| 2003/0225318 A1 | 12/2003 | Montegrande et al. | |
| 2004/0059248 A1 | 3/2004 | Messner et al. | |
| 2004/0073137 A1 | 4/2004 | Lloyd et al. | |
| 2004/0111050 A1 | 6/2004 | Smedley et al. | |
| 2004/0116794 A1 | 6/2004 | Fink et al. | |
| 2004/0186367 A1 | 9/2004 | Fresco | |
| 2004/0254438 A1 | 12/2004 | Chuck et al. | |
| 2005/0049578 A1 | 3/2005 | Tu et al. | |
| 2005/0159660 A1 | 7/2005 | Montegrande et al. | |
| 2005/0271704 A1 | 12/2005 | Tu et al. | |
| 2005/0273033 A1 | 12/2005 | Grahn et al. | |
| 2006/0131350 A1 | 6/2006 | Schechter et al. | |
| 2007/0106199 A1 | 5/2007 | Krivoy et al. | |
| 2007/0109117 A1 | 5/2007 | Heitzmann et al. | |
| 2007/0123767 A1 | 5/2007 | Montegrande et al. | |
| 2007/0129623 A1 | 6/2007 | Fleischmann et al. | |
| 2007/0212397 A1 | 9/2007 | Roth | |
| 2008/0015421 A1 | 1/2008 | Penner | |
| 2008/0039792 A1 * | 2/2008 | Meng et al. | 604/114 |
| 2008/0125691 A1 | 5/2008 | Yaron et al. | |
| 2008/0129486 A1 | 6/2008 | Jeckelmann et al. | |
| 2008/0228127 A1 | 9/2008 | Burns et al. | |
| 2009/0069648 A1 | 3/2009 | Irazqui et al. | |
| 2009/0076367 A1 | 3/2009 | Sit et al. | |
| 2009/0227933 A1 | 9/2009 | Karageozian | |
| 2009/0275924 A1 | 11/2009 | Lattanzio et al. | |
| 2009/0312742 A1 | 12/2009 | Pang et al. | |
| 2010/0010416 A1 | 1/2010 | Juan, Jr. et al. | |
| 2010/0042209 A1 | 2/2010 | Guarnieri | |
| 2010/0121348 A1 | 5/2010 | Van Der Burg et al. | |
| 2010/0234717 A1 | 9/2010 | Wismer | |
| 2010/0253167 A1 | 10/2010 | Charnley et al. | |
| 2011/0071458 A1 * | 3/2011 | Rickard | 604/9 |
| 2011/0071459 A1 | 3/2011 | Rickard et al. | |

FOREIGN PATENT DOCUMENTS

| | | |
|---|---|---|
| WO | WO 9805084 | 2/1998 |
| WO | WO 01/94784 | 12/2001 |
| WO | WO 03/001991 | 1/2003 |
| WO | WO 03/102632 | 12/2003 |
| WO | WO 2007/136993 | 11/2007 |
| WO | WO 2007127305 | 11/2007 |
| WO | WO 2009/026499 | 2/2009 |
| WO | WO 2009/049686 | 4/2009 |
| WO | WO 2011034742 A2 * | 3/2011 |

OTHER PUBLICATIONS

Eggers, T., et al, "Wireless Intra-Ocular Pressure Monitoring System Integrated Into an Artificial Lens," 1st Annual Int'l IEEE-EMBS Special Topic Conference on Microtechnologies in Medicine & Biology, Oct. 12-14, 2000, pp. 466-469, Lyon, France.

Greene, M.E. and Gilman, B.G., "Intraocular Pressure Measurement With Instrumented Contact Lenses," Investigative Ophthalmology & Visual Science (IVOS), Apr. 1974, pp. 299-302, vol. 13, No. 4, IVOS.
Hjortdal, Jesper and Jensen, Peter, "In Vitro Measurement of Corneal Strain, Thickness, and Curvature Using Digital Image Processing," Acta Ophthalmologica Scandinavica, 1995, pp. 5-11, vol. 73, Denmark.
International Searching Authority, Search Report and Written Opinion of the International Searching Authority, PCT/US2010/033329, Jul. 13, 2010, 14 pages.
International Searching Authority, Search Report and Written Opinion of the International Searching Authority, PCT/US2010/047429, Nov. 1, 2010, 15 pages.
International Searching Authority, Search Report and Written Opinion of the International Searching Authority, PCT/US2010/047600, Dec. 14, 2010, 13 pages.
International Searching Authority, Search Report and Written Opinion of the International Searching Authority, PCT/US2010/049424, Nov. 26, 2010, 15 pages.
International Searching Authority, Search Report of the International Searching Authority, PCT/US2011/036742, Aug. 17, 2011, 2 pages.
Lam, Andrew K.C. and Douthwaite, William A., "The Effect of an Artificially Elevated Intraocular Pressure on the Central Corneal Curvature," Ophthalmic and Physiological Optics, 1997, pp. 18-24, vol. 17, No. 1, Elsevier Science, Ltd., Great Britain.
Leonardi, Matteo, et al., "A Soft Contact Lens With a Mems Strain Gage Embedded for Intraocular Pressure Monitoring," In Proc. 12th Int'l Conference on Solid State Sensors, Actuators and Microsystems, Jun. 8-12, 2003, pp. 1043-1046, vol. 2, Boston, MA.
Leonardi, Matteo, et al., "First Steps Toward Noninvasive Intraocular Pressure Monitoring with a Sensing Contact Lens," Investigative Ophthalmology & Visual Science (IVOS), 2004, pp. 3113-3117, vol. 45, No. 9, IVOS.
McLaren, Jay W., et al, "Continuous Measurement of Intraocular Pressure in Rabbits by Telemetry," Investigative Ophthalmology & Visual Science (IVOS), May 1996, pp. 966-975, vol. 37, No. 6, IVOS.
Mokwa, Wilfried, et al, "Micro-Transponder Systems for Medical Applications," IEEE Transactions on Instrumentation and Measurement, Dec. 2001, pp. 1551-1555, vol. 50, No. 6, IEEE, Germany.
Puers, Robert, "Linking Sensors with Telemetry: Impact on the System Design," In Proc. 8th Int'l Conference of Solid State Sensors, Actuators, Eurosens, Jun. 25-29, 1995, pp. 169-174, Stockholm, Sweden.
Schnakenberg, U., et al, "Initial Investigations on Systems for Measuring Intraocular Pressure," Sensors and Actuators, 2000, pp. 287-291, vol. 85, Elsevier Science B.V., Germany.
Stangel, Karsten, et al, "A Programmable Intraocular CMOS Pressure Sensor System Implant," IEEE Journal of Solid-State Circuits, Jul. 2001, pp. 1094-1100, vol. 36, No. 7, IEEE, Germany.
Ullerich, Stella, et al, "Micro Coils for an Advanced System for Measuring Intraocular Pressure," 1st Annual Int'l IEEE-EMBS Special Topic Conference on Microtechnologies in Medicine & Biology, Oct. 12-14, 2000, pp. 470-474, Lyon, France.
Van Schuylenbergh, K., et al, "An Implantable Telemetric Tonometer for Direct Intraocular Pressure Measurements," 1st European Conference on Biomedical Engineering, Feb. 1991, pp. 194-195, vol. 17, No. 20, Nice, France.
"Walter, Peter; Intraocular Pressure Sensor: Where Are We—Where Will We Go? Journal Graefe's Archive for Clinical and Experimental Ophthalmology; Publisher Springer Berline/Heidelberg; ISSN 0721-832X (Print) 1435-702X (Online); Issue vol. 240, No. 5/May 2002 DOI 10.1007/s00417-002-0474-y; pp. 335-336; Subject Collection Medicine.".
International Search Report and Written Opinion issued for PCT/US2012/067722 dated Dec. 6, 2013, 8 pgs.

* cited by examiner

BUBBLE-DRIVEN IOP CONTROL SYSTEM

BACKGROUND

The present disclosure relates generally to valves and associated systems and methods for use in ophthalmic treatments. In some instances, embodiments of the present disclosure are configured to be part of an IOP control system.

Glaucoma, a group of eye diseases affecting the retina and optic nerve, is one of the leading causes of blindness worldwide. Most forms of glaucoma result when the intraocular pressure (TOP) increases to pressures above normal for prolonged periods of time. IOP can increase due to high resistance to the drainage of the aqueous humor relative to its production. Left untreated, an elevated IOP causes irreversible damage to the optic nerve and retinal fibers resulting in a progressive, permanent loss of vision.

The eye's ciliary body continuously produces aqueous humor, the clear fluid that fills the anterior segment of the eye (the space between the cornea and lens). The aqueous humor flows out of the anterior chamber (the space between the cornea and iris) through the trabecular meshwork and the uveoscleral pathways, both of which contribute to the aqueous drainage system. The delicate balance between the production and drainage of aqueous humor determines the eye's IOP.

FIG. 1 is a diagram of the front portion of an eye that helps to explain the processes of glaucoma. In FIG. 1, representations of the lens 110, cornea 120, iris 130, ciliary body 140, trabecular meshwork 150, and Schlemm's canal 160 are pictured. Anatomically, the anterior segment of the eye includes the structures that cause elevated IOP which may lead to glaucoma. Aqueous fluid is produced by the ciliary body 140 that lies beneath the iris 130 and adjacent to the lens 110 in the anterior segment of the eye. This aqueous humor washes over the lens 110 and iris 130 and flows to the drainage system located in the angle of the anterior chamber. The angle of the anterior chamber, which extends circumferentially around the eye, contains structures that allow the aqueous humor to drain. The trabecular meshwork 150 is commonly implicated in glaucoma. The trabecular meshwork 150 extends circumferentially around the anterior chamber. The trabecular meshwork 150 seems to act as a filter, limiting the outflow of aqueous humor and providing a back pressure that directly relates to IOP. Schlemm's canal 160 is located beyond the trabecular meshwork 150. Schlemm's canal 160 is fluidically coupled to collector channels (not shown) allowing aqueous humor to flow out of the anterior chamber. The two arrows in the anterior segment of FIG. 1 show the flow of aqueous humor from the ciliary bodies 140, over the lens 110, over the iris 130, through the trabecular meshwork 150, and into Schlemm's canal 160 and its collector channels.

One method of treating glaucoma includes implanting a drainage device in a patient's eye. The drainage device allows fluid to flow from the interior chamber of the eye to a drainage site, relieving pressure in the eye and thus lowering IOP. These devices are generally passive devices and do not provide a smart, interactive control of the amount of flow through the drainage tube. In addition, fluid filled blebs frequently develop at the drainage site. The development of the bleb typically includes fibrosis, which leads to increased flow resistance and it is generally the case that this resistance increases overtime. This development and progression of fibrosis reduces or eliminates flow from the anterior chamber, eliminating the capacity of the drainage device to affect IOP.

The system and methods disclosed herein overcome one or more of the deficiencies of the prior art.

SUMMARY

In one exemplary aspect, the present disclosure is directed to an IOP control system for implantation in an eye of a patient to provide drainage from an anterior chamber of the eye to a drainage location at the eye. The system may include a drainage tube with a first end configured to be located in the anterior chamber of an eye and a second end. The tube may be configured to convey fluid from the anterior chamber toward the drainage location to relieve IOP. A valve system in fluid communication with the drainage tube may be configured for implantation in the eye. The valve system may be arranged to control drainage flow through the drainage tube between the anterior chamber and the drainage site. The valve system may be configured to control fluid flow using an electrolysis process.

In another exemplary aspect, the present disclosure is directed to an IOP control system for implantation in an eye of a patient to provide drainage from an anterior chamber of the eye to a drainage location at the eye. It includes a drainage tube with a first end configured to be located in an anterior chamber of an eye, with the tube being configured to convey fluid from the anterior chamber. The IOP control system may also include a first sensor configured to detect pressure in the anterior chamber, a second sensor configured to detect atmospheric pressure, and a third sensor configured to detect pressure at the drainage site. A valve system may be in fluid communication with the drainage tube and may be configured for implantation in the eye. The valve system may be arranged to control drainage flow through the drainage tube between the anterior chamber and the drainage site. A processor may be in communication with and configured to receive data from the first, second, and third sensors. The processor may be configured to control the valve system based on the received data to maintain desired pressures in the anterior chamber and at the drainage site.

In yet another exemplary aspect, the present disclosure is directed to a method performed by an IOP control system that drains fluid from an anterior chamber of the eye to a drainage location of the eye. The method may include detecting pressure within an anterior chamber of the eye, detecting pressure at a drainage location of the eye, and determining whether to adjust drainage fluid flow based on the detected pressures by comparing the detected pressures in both the anterior chamber and the drainage location to preestablished acceptable pressures or pressure profiles as a function of time. The method may also include adjusting drainage fluid flow from the anterior chamber using a valve system to achieve pressures in both the anterior chamber and the drainage location corresponding to the acceptable pressures or pressure profiles as a function of time.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

The accompanying drawings illustrate embodiments of the devices and methods disclosed herein and together with the description, serve to explain the principles of the present disclosure.

DETAILED DESCRIPTION OF THE PREFERRED EMBODIMENTS

Figure 1:
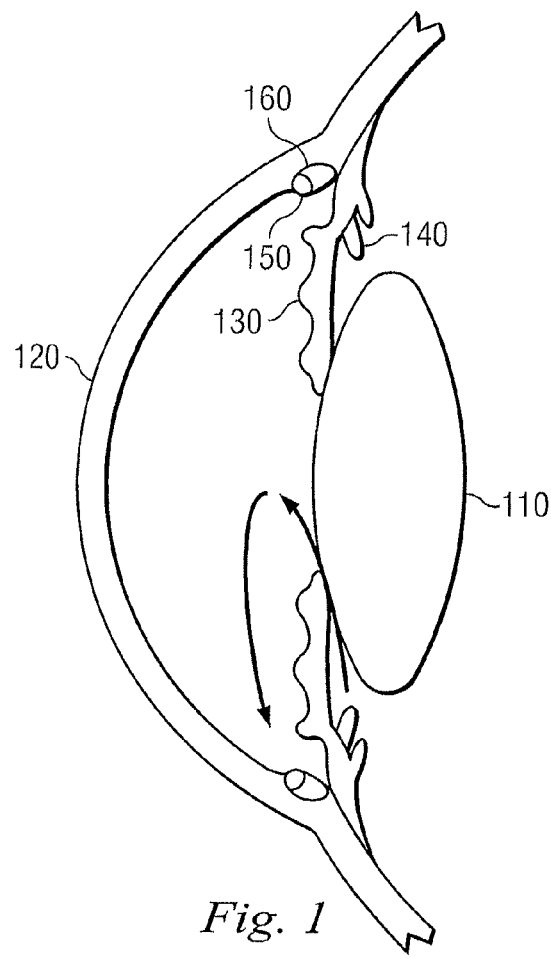
FIG. 1 is a diagram of the front portion of an eye.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For simplicity, in some instances the same reference numbers are used throughout the drawings to refer to the same or like parts.

In some particular instances, embodiments of the present disclosure are configured to be part of the glaucoma drainage devices disclosed in U.S. patent application Ser. No. 12/832,449, filed Jul. 8, 2010 and U.S. patent application Ser. No. 12/837,803, filed Jul. 16, 2010, which are a continuation-in-part applications of U.S. application Ser. No. 12/685,772 filed Jan. 12, 2010, which is a continuation-in-part of U.S. application Ser. No. 12/609,043 filed Oct. 30, 2009, which is a continuation-in-part of U.S. application Ser. No. 12/563,244 filed Sep. 21, 2009, each of which is hereby incorporated by reference in its entirety.

Figure 2:
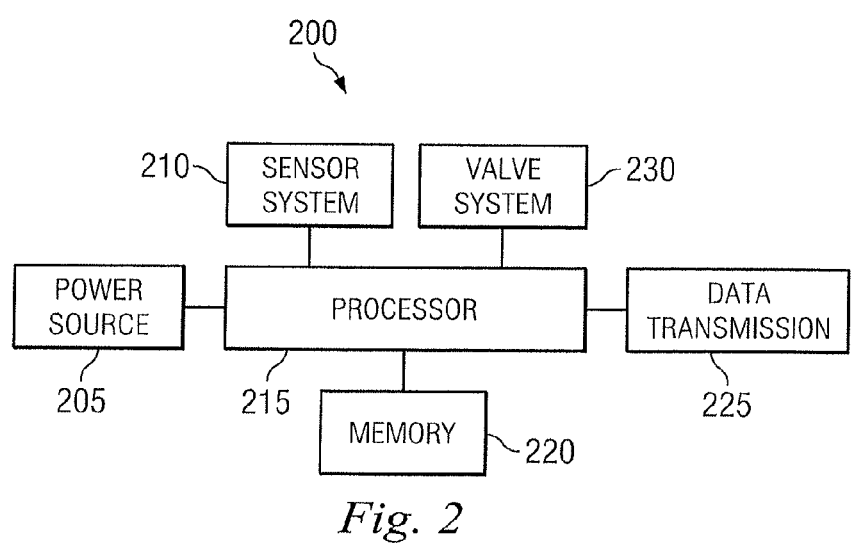
FIG. 2 is a block diagram of an exemplary IOP control system according to the principles of the present disclosure.

FIG. 2 is a block diagram of an exemplary IOP control system 200 implantable in an eye of a patient for the treatment of glaucoma or other conditions. The IOP control system 200 is configured in a manner that provides IOP pressure control, but also regulates and controls bleb pressures, reducing complications arising from surgical implant glaucoma treatments. In FIG. 2, the IOP control system 200 includes a power source 205, an IOP sensor system 210, a processor 215, a memory 220, a data transmission module 225, and a valve system 230.

The power source 205 is typically a rechargeable battery, such as a lithium ion or lithium polymer battery, although other types of batteries may be employed. In addition, any other type of power cell is appropriate for power source 205. Power source 205 provides power to the system 200, and more particularly to processor 215. Power source can be recharged via inductive coupling such as an RFID link or other type of magnetic coupling.

Processor 215 is typically an integrated circuit with power, input, and output pins capable of performing logic functions. In various embodiments, processor 215 is a targeted device controller. In such a case, processor 215 performs specific control functions targeted to a specific device or component, such as a data transmission module 225, power source 205, sensing system 210, valve system 230, or memory 220. In other embodiments, processor 215 is a microprocessor. In such a case, processor 215 is programmable so that it can function to control more than one component of the device. In other cases, processor 215 is not a programmable microprocessor, but instead is a special purpose controller configured to control different components that perform different functions.

Memory 220 is typically a semiconductor memory such as RAM, FRAM, or flash memory. Memory 220 interfaces with processor 215. As such, processor 215 can write to and read from memory 220. For example, processor 215 can be configured to read data from the IOP sensor system 210 and write that data to memory 220. In this manner, a series of IOP readings can be stored in memory 220. Processor 215 is also capable of performing other basic memory functions, such as erasing or overwriting memory 220, detecting when memory 220 is full, and other common functions associated with managing semiconductor memory.

Data transmission module 225 may employ any of a number of different types of data transmission. For example, data transmission module 225 may be an active device such as a radio. Data transmission module 225 may also be a passive device such as the antenna on an RFID tag. In this case, an RFID tag includes memory 220 and data transmission module 225 in the form of an antenna. An RFID reader can then be placed near the system 200 to write data to or read data from memory 220. Since the amount of data typically stored in memory 220 is likely to be small (consisting of IOP readings over a period of time), the speed with which data is transferred is not crucial. Other types of data that can be stored in memory 220 and transmitted by data transmission module 225 include, but are not limited to, power source data (e.g. low battery, battery defect), speaker data (warning tones, voices), IOP sensor data (IOP readings, problem conditions), time stamp data and the like.

Alternatively, data transmission module 225 may be activated to communicate an elevated IOP condition to a secondary device such as a PDA, cell phone, computer, wrist watch, custom device exclusively for this purpose, remote accessible data storage site (e.g. an internet server, email server, text message server), or other electronic device. In one embodiment, a personal electronic device uploads the data to the remote accessible data storage site (e.g. an internet server, email server, text message server). Information may be uploaded to a remote accessible data storage site so that it can be viewed in real time, for example, by medical personnel. For example, in a hospital setting, after a patient has undergone glaucoma surgery and had system 200 implanted, a secondary device may be located next to the patient's hospital bed. Since IOP fluctuations are common after glaucoma surgery (both on the high side and on the low side which is also a dangerous condition), processor 215 can read IOP measurements made by an implanted IOP sensor 210. If processor 215 reads an unsafe IOP condition, data transmission module 225 can alert the patient and medical staff directly or by transmitting the unsafe readings to a secondary device. The IOP sensor system 210 is described below with reference to FIGS. 3 and 4, and the valve system 230 is described below with reference to FIG. 5.

Figure 3:
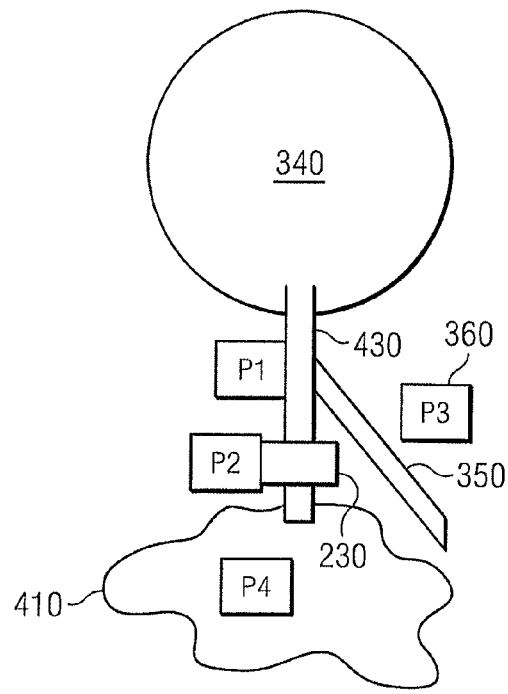
FIG. 3 is a schematic diagram of an exemplary IOP control system according to the principles of the present disclosure.

FIG. 3 is a diagram of the exemplary IOP sensor system 210, a drainage tube 430, the valve system 230, and a divider 350. In FIG. 3, the exemplary IOP sensor system 210 includes four pressure sensors, P1, P2, P3, and P4. Pressure sensor P1 is located in or is in fluidic communication with the anterior chamber 340, pressure sensor P2 is located to measure intermediate pressures found within the valve system 230, pressure sensor P3 is located remotely from P1 and P2 in manner to measure atmospheric pressure, and the pressure sensor P4 is located at a drainage site in the subconjunctival space and is arranged to measure bleb pressure. In some embodiments, pressure sensor P1 is located in a lumen or tube that is in fluid communication with the anterior chamber.

The drainage tube 430 drains aqueous from the anterior chamber 340 of the eye. The valve system 230 controls the flow of aqueous through the tube 430. In the embodiment shown, the pressure sensor P1 measures the pressure in the tube 430 upstream from the valve system 230 and downstream from the anterior chamber 340. In this manner, pressure sensor P1 measures the pressure in the anterior chamber 340. The expected measurement discrepancy between the true anterior chamber pressure and that measured by P1 when located in a tube downstream of the anterior chamber (even when located between the sclera and the conjunctiva) is very minimal. For example, Poiseuille's law for pipe flow predicts a pressure drop of 0.01 mmHg across a 5-millimeter long tube with a 0.300 millimeter inner diameter for a flow rate of 3 microliters per minute of water.

In some embodiments, the divider 350 separates pressure sensor P4 from pressure sensor P3. Pressure sensor P4 is located at a drainage site (e.g. 410 in FIG. 4). As such, pressure sensor P4 may be located in a pocket, such as a bleb, that generally contains aqueous or in communication with such a pocket, via a tube for example, and is in a wet location 410. The drainage site 410 may be, for example, in a subconjunctival space, a suprachoroidal space, a subscleral space, a supraciliary space, Schlemm's canal, a collector channel, an episcleral vein, and a uveo-scleral pathway, among other locations in the eye.

In some embodiments, the system includes barriers that separate the sensors P1, P2, P3, and P4. these barriers may be elements of the system itself. In FIG. 3, the pressure sensor P3 is physically separated from pressure sensor P4 by the divider 350. Divider 350 is a physical structure that separates the wet location 410 of P4 from the dry location 360 of P3. In one example, the barrier separating anterior chamber pressure sensor P1 and the drainage site pressure sensor P4 is the valve system 230. In some examples, as described above, the IOP control system 200 is formed as a glaucoma drainage device plate. In this example, the atmospheric sensor P3 resides on a top of the plate with a barrier preventing it from being crushed while still allowing pressure communication, such as through the conjunctiva. Drainage site sensor P4 may then reside on the bottom in direct contact with the drainage site.

In one example, dividers such as the divider 350 are included when the system of the present invention is located on a single substrate. In this configuration, all four pressure sensors (P1, P2, P3, and P4) are located on a substrate that includes tube 430, valve system 230, divider 350, and the other components of the system. Note that divider 350 may take many forms, such as but not limited to a tube fluidically coupling pressure sensor P3 to a site away from the substrate or as a pocket residing on the top portion of the substrate away from and fluidically independent of the drainage site.

In some embodiments of the present invention, the atmospheric pressure sensor P3 is located in close proximity to the eye, and in one embodiment, the pressure sensor P3 may be implanted in the eye under the conjunctiva. In such a case, pressure sensor P3 measures a pressure that can be correlated with atmospheric pressure. For example, true atmospheric pressure can be a function of the pressure reading of pressure sensor P3. Pressure sensor P3 may also be located in a dry portion 360 of the subconjunctival space, separate from the drainage location. In one embodiment, the atmospheric pressure sensor P3 is disposed on a top of a standard glaucoma drainage device (GDD) plate, while the drainage site pressure sensor P4 resides on a bottom of the GDD plate in direct contact with the drainage site. Accordingly, the GDD plate acts as a physical barrier separating pressure P3 and P4. In this embodiment, a barrier may be disposed on the GDD plate to prevent the sensor P3 from being crushed, while still allowing pressure communication through the conjunctiva. Regardless of location, pressure sensor P3 is intended to measure atmospheric pressure in the vicinity of the eye or at the eye's surface.

Generally, IOP is a gauge pressure reading—the difference between the absolute pressure in the eye (as measured by P1) and atmospheric pressure (as measured by P3). Atmospheric pressure, typically about 760 mm Hg, often varies in magnitude by 10 mmHg or more depending on weather conditions or indoor climate control systems. In addition, the effective atmospheric pressure can vary significantly—in excess of 100 mmHg—if a patient goes swimming, hiking, riding in an airplane, etc. Such a variation in atmospheric pressure is significant since IOP is typically in the range of about 15 mm Hg. Thus, for accurate monitoring of IOP, it is desirable to have pressure readings for the anterior chamber (as measured by P1) and atmospheric pressure in the vicinity of the eye (as measured by sensor P3).

Therefore, in one embodiment of the present invention, pressure readings are taken by pressure sensors P1 and P3 simultaneously or nearly simultaneously over time so that the actual IOP can be calculated (as P1-P3 or P1-f(P3), where f(P3) indicates a function of P3). The pressure readings of P1 and P3 can be stored in memory 220 by processor 215. They can later be read from memory so that actual IOP over time can be interpreted by a physician.

Pressure sensors P1, P2, P3, and P4 can be any type of pressure sensors suitable for implantation in the eye. They each may be the same type of pressure sensor, or they may be different types of pressure sensors. For example, pressure sensors P1, P2, and P4 may be the same type of pressure sensor (implanted in the eye), and pressure sensor P3 may be a different type of pressure sensor (in the vicinity of the eye).

Figure 4:
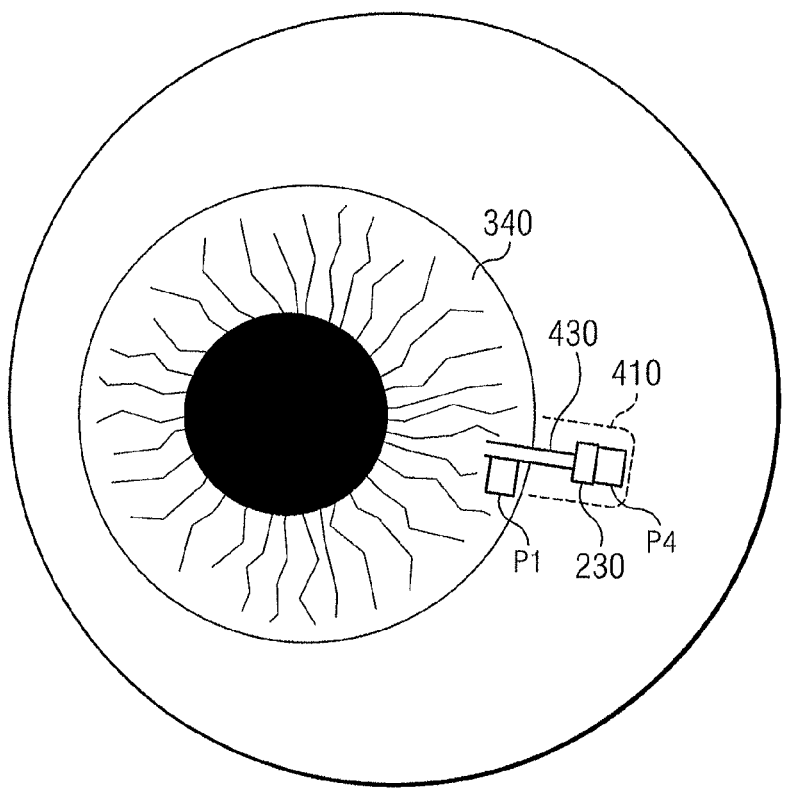
FIG. 4 is an illustration showing one possible application of the IOP sensor of the present disclosure.

In another embodiment of the present invention, pressure readings taken by pressure sensors P1, P2, and P4 can be used to control a device that drains aqueous from the anterior chamber 340. FIG. 4 is a diagram of one possible application of the sensors in a system utilizing the readings of pressures sensors P1-P4. In FIG. 4, pressure sensor P1 measures the pressure in the anterior chamber 340 of the eye. Pressure sensor P4 measures the pressure at a drainage site 410.

The drainage tube 430 may be arranged to shunt fluid from the anterior chamber 340 to the drainage location 410, which may be placed at any of numerous locations within the eye. For example, some tubes are arranged to shunt aqueous from the anterior chamber 340 to the subconjunctival space thus forming a bleb under the conjunctiva or alternatively, to the subscleral space thus forming a bleb under the sclera. Other tube designs shunt aqueous from the anterior chamber to the suprachoroidal space, the supraciliary space, the juxta-uveal space, or to the choroid, forming blebs in those respective locations. In other applications, the drainage tube shunts aqueous from the anterior chamber to Schlemm's canal, a collector channel in Schlemm's canal, or any of a number of different blood vessels like an episcleral vein. In some examples, the drainage tube even shunts aqueous from the anterior chamber to outside the conjunctiva. Each of these different anatomical locations to which aqueous is shunted is an example of a drainage location 410. Other examples of a drainage location 410 include, but are not limited to: a subconjunctival space, a suprachoroidal space, a subscleral space, a supraciliary space, Schlemm's canal, a collector channel, an episcleral vein, and a uveo-scleral pathway.

In FIG. 4, the tube 430 with the valve system 230 on one end is located with one end in the anterior chamber 340 and the other end in the drainage location 410. The valve system 230 controls the flow of aqueous from the anterior chamber 340 to drainage location 410. As indicated above, the pressure sensor P1 is located in the anterior chamber or in fluid communication with the anterior chamber 340, and therefore, as shown in the embodiment of FIG. 3, pressure sensor P1 is located upstream from valve system 230. In this manner, in some examples, pressure sensor P1 is located in the subconjunctival space but is in fluid communication with the anterior chamber 340. As indicated above, in some examples, the pressure sensor P1 is disposed within the tube 430, before the valve system 230. In other examples, the pressure sensor P1 is disposed within the anterior chamber itself.

Since pressure sensor P1 measures the pressure in the anterior chamber 340 and pressure sensor P4 measures pressure at the drainage location 410, the difference between the readings taken by these two pressure sensors (P1-P4) provides an indication of the pressure differential between the anterior chamber 340 and the drainage location 410. In one embodiment, this pressure differential dictates the rate of aqueous flow from the anterior chamber 340 to the drainage location 410.

One complication involved with surgery that shunts the anterior chamber 340 to a drainage location 410 is hypotony—a dangerous drop in IOP that can result in severe consequences. It is desirable to control the rate of aqueous outflow from the anterior chamber 340 to the drainage location 410 so as to prevent hypotony. Readings from pressure sensors P1, P2, P3, and P4 can be used to control the flow rate through tube 430 by controlling the valve system 230. For example, the valve system 230 can be controlled based on the pressure readings from pressure sensors P1, P2, P3, and P4.

In another embodiment of the present invention, IOP (based on readings from pressure sensor P1 and pressure sensor P3) can be controlled by controlling valve system 230. In this example, IOP is the control parameter. To accomplish this, the valve system 230 can be adjusted to maintain a particular IOP (like an IOP of 15 mm Hg). Valve system 230 may be opened at desirable times, such as, for example, more at night than during the day to maintain a particular IOP. In other embodiments, an IOP drop can be controlled by the valve system 230. Immediately after surgery, IOP can drop precipitously. Valve system 230 can be adjusted to permit a gradual drop in IOP based on readings from pressure sensors P1 and P3. Note that the physician would be able to set the high/low IOP thresholds wirelessly to meet each patients specific requirements.

In another embodiment of the present invention, readings from pressure sensor P4 (or from the difference between pressure sensor P4 and atmospheric pressure as measured by P3) can be used to control valve system 230 so as to control the morphology of a bleb. One of the problems associated with implant surgery is bleb failure. A bleb can fail due to poor formation or fibrosis. The pressure in the bleb is one factor that determines bleb morphology. As explained above, too much pressure can cause a bleb to migrate to an undesirable location or can lead to fibrosis. The pressure of the bleb can be controlled by using the reading from pressure sensor P4 (at drainage location 410—in this case, a bleb). In one embodiment of the present invention, the difference between the pressure in the bleb (as measured by P4) and atmospheric pressure (as measured by P3) can be used to control valve system 230 to maintain a desired bleb pressure. In this manner, the IOP pressure sensor of the present invention can also be used to properly maintain a bleb.

Valve system 230 may be controlled by microprocessor 215 based on input data received from the sensors. A desired pressure differential (that corresponds to a desired flow rate) can be maintained by controlling the operation of valve system 230. Likewise, a desired IOP, IOP change rate, or bleb pressure can be controlled by controlling the operation of valve system 230.

Figure 5:
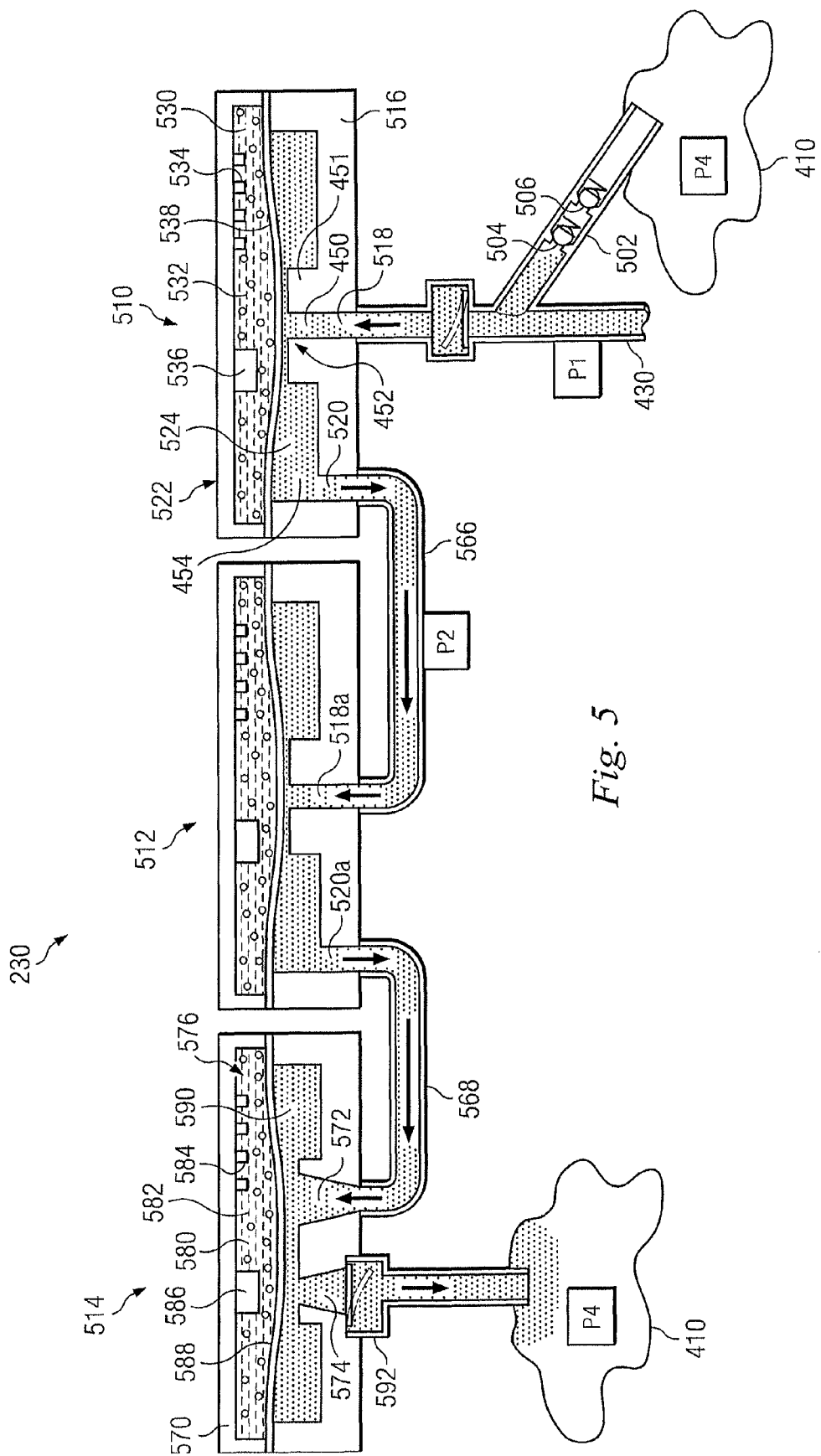
FIG. 5 is an illustration of a cross-sectional view of an exemplary valve system according to one embodiment consistent with the principles of the present disclosure.

FIG. 5 shows an exemplary embodiment of the valve system 230 in greater detail. The valve system 230 is disposed along, and may form a part of, the drainage tube 430 between the tube end in the anterior chamber and the drainage site.

The valve system 230 is configured to control the flow of drainage fluid through the drainage line, and thereby control pressure in the eye, including the IOP. For example, when IOP is high, the valve system 230 may operate to permit increased flow through the drainage tube, and when IOP is low, the valve system 230 may operate to decrease the flow through the drainage tube. In addition, the valve system 230 is configured to monitor and control the flow of drainage fluid to the bleb, and thereby control the bleb pressure to maintain a desired fluid flow to the bleb. This may decrease fibrosis and increase absorption efficiency. To accomplish this, the valve system 230 is responsive to signals sent as instructions from the processor 215. The processor 215 is responsive to pressure measurements taken by the pressure sensors P1, P2, P3, and P4, and/or the IOP as determined by detected pressures, as explained above.

In the example in FIG. 5, the valve system 230 includes a main control valve 510, a secondary control valve 512, and a pump 514. Fluid flows from the drainage tube 430 to the main control valve 510, through the main control valve 510 to the secondary control valve 512, and then to the pump 514. The fluid may exit the pump 514 to the drainage site 410 or may flow through additional tubing lengths to the drainage site 410.

Referring now to FIG. 5, the main control valve 510 includes a housing 516 with an entrance port 518 and an exit port 520, a flow control system 522 in the housing 516, and a fluid flow passageway 524 extending between the entrance port 518 and the exit port 520. The entrance port 518 connects to the drainage tube 430 and is configured to receive aqueous flowing from the drainage tube 430. The exit port 520 permits fluid to exit the housing 516 for release at the drainage site 410 or for further regulation.

The main control valve 510 includes a flow control chamber 530, an actuator fluid 532 in the flow control chamber 530, electrodes 534 arranged to cooperate with the actuator fluid 532, an optional diffusion barrier 536 in the flow control chamber 530, and a flexible membrane 538. In operation the electrodes 534 generate bubbles in the actuator fluid 532 through electrolysis, increasing the pressure within the chamber of the flow control chamber 530. As the pressure increases, the flexible membrane 538 expands into the fluid flow passageway 524, decreasing the cross-sectional area of the fluid flow passageway 524, thereby restricting some fluid flow from the drainage tube 430. In a similar, but opposite manner, as the solution in the flow control chamber 530 returns to its more fluid state, the volume in the chamber 530 decreases, permitting the flexible membrane 538 to move further out of the fluid flow passageway 524, thereby permitting an increased level of fluid flow from the drainage tube 430 through the passageway 524.

As can be seen in FIG. 5, in the example shown, the flow control chamber 530 is formed in the housing 516 with rigid structure on three sides. The chamber 530 is sealed closed by the flexible membrane 538. Accordingly, as volume increases, the pressure increase acts to displace the membrane 538 in only one direction. However, in other embodiments, the flow control chamber 530 may be formed of less rigid materials, and expansion may occur in more than one direction. In accordance, with this, in some examples the fluid flow passageway 524 includes flexible membrane material that may displace to affect fluid flow through the passageway from more than one direction. In some examples, the flexible membrane 538 acts as a toroid or sphincter, with the passageway extending through the hollow center or orifice. In other examples the flexible membrane 538 is disposed on two sides of the passageway. In some of these examples the sides are on opposing sides of the passageway. Some of these embodiments may have two or more separate flexible membranes that cooperate to limit the cross-sectional area of the fluid flow passageway 524.

The flexible membrane 538 may be formed of an elastically deformable elastomeric including without limitation, materials such as a silicone, silicon nitride, silicone elastomeric, polyimide, parylene and others. In the example shown, the flexible membrane 538 is secured to the housing 516 at its edges. Although shown in cross section, the flow control chamber 530 may be disposed to form a circular or cylindrical chamber, with the flexible membrane 538 being secured along the diameter. Accordingly, the flexible membrane 538 may be a circular material secured at its periphery to the housing 516. As such, as the volume or pressure increases within the chamber, the central portion of the flexible membrane provides the highest level of displacement. In other embodiments, the housing and flexible membrane are formed so that the membrane has a non-circular shape, including oval, substantially rectangular, or square, for example. Other shapes are also contemplated. Applicable to all flexible membranes such as 538 may also have corrugation features (such as ridges and valleys), whose depths will effect the displacement shape.

The actuator fluid 532 is contained in the flow control chamber 530 and in some embodiments includes water. Some embodiments include a saline component like sodium chloride in the water.

The electrodes 534 are disposed within the actuator fluid 532 in a manner permitting at least a portion of the ions and electrolytes in the actuator fluid 532 to allow an actuating potential to drive an electrochemical reaction, forming bubbles through electrolysis, with an overall result of a phase change from liquid to gas for a portion of the fluid. As this occurs, the pressure in the chamber increases, thereby increasing overall pressure. This increased pressure acts on the flexible membrane 538 to cause its displacement. The electrodes are in electrical communication with the power source 205, which is controlled by the processor 215. Through the electrolysis, some of the water in the actuator fluid 532 may be converted into hydrogen and oxygen molecules. In the exemplary embodiment shown the electrodes 534 are interdigitated for efficient and effective electrolysis.

The diffusion barrier 536 within the chamber 530 includes a plurality of small passageways that permit the passage of fluid, but that increases the diffusion pathway and that may trap or capture gas molecules. This slows the recombination of these molecules, once the molecules are phase-changed from liquid to gas. Accordingly, at least a portion of the actuator fluid may be held in a gaseous state for a sufficient length of time to provide regulatory control of the drainage fluid through the passageway in the valve without a continuous application of energy to the system, thereby reducing the amount of energy required.

In the example shown, the passageway 524 includes a first portion 450 extending through a boss 451 that is arranged to cooperate with the flow control system 522 to control drainage fluid flow at a control region 452, and a second, larger portion 454 configured in the embodiment shown as a chamber adjacent the boss 451, that less actively impacts the flow through the main control valve 510. In this example the control region 452 is disposed adjacent the central area of the flexible membrane 538. In accordance with this, the first portion 450 of the fluid flow passageway 524 is formed to be substantially perpendicular to the general plane of the flexible membrane 538, and the upper surface of the boss 451 is arranged to be substantially parallel to the general plane of the flexible membrane 538. As such, flow through the first portion 450 is directed in the direction of and directly at the flexible membrane 538. Because of this, the drainage fluid is forced to redirect at an angle of about 90 degrees, although other angles are contemplated. Because of this arrangement, the flexible membrane 538 in this exemplary embodiment can more easily displace only slightly, but still provide a significant modification in the drainage flow. This occurs because the flexible membrane 538 may act in some respects as a cap on the first portion 450 of the fluid flow passageway. In some aspects, the flexible membrane 538 is arranged to cover the entire upper surface of the boss 451, and may even stretch to extend at least partially along the sides of the boss 451 adjacent the edge between the top of the boss 451 and the sides. Accordingly, in such embodiments, the flexible membrane 538 may largely limit or entirely cut off flow through the primary control valve 510.

The second portion 454 of the fluid flow passageway 524 is configured in some respects as a chamber adjacent the boss 451, having a much larger volume. Accordingly, although the second portion 454 of the passageway 524 extends along a portion of the flexible membrane 538, displacement of the membrane does not have as significant an effect on the drainage fluid flow. Accordingly, in this embodiment, the drainage fluid flow is controlled primarily at the control region, along the top of the boss 451, which in this embodiment is disposed at the central part of the membrane 538.

In the example shown in FIG. 5, the valve system 230 includes the secondary control valve 512. Here, the secondary control valve 512 is structurally similar to the main control valve 510, and it will not be re-described in great detail. It is sufficient to note that when referring to elements of the secondary control valve 512, the present disclosure will refer to those items with the same reference numeral as the main control valve, but with the suffix a. It is worth noting that the secondary control valve may be a valve of a different type than the main control valve 512. For example, the secondary control valve may be a pressure controlled valve or a different type of an electronically controlled valve. Different types of pumps, whether electronically controlled or whether pressure controlled, also may be used in place of the pump 514. In the example shown in FIG. 5, the secondary control valve 512 includes an entrance port 518*a* and an exit port 520*a*. The entrance port 518*a* is in fluid communication with the exit port 520 of the main control valve 510. Although shown as being connected by a tube 566, some embodiments do not have a tube, but instead the valves 510, 512 are disposed so that the fluid flows directly from one port to another, and in some embodiments, the main control valve and the secondary control valve may share the same housing. In some embodiments tube 566 may be a rigid or flexible flow channel formed by the substrate housing the valves.

Pressure at the exit port 520 is detected via the pressure sensor P2. Fluid then flows into the secondary control valve 512. In some examples, the secondary control valve 512 is controlled based on the interplay with a signal relating pressure at sensor P2 to the bleb pressure at sensor P4 and to atmospheric pressure detected by sensor P3 to prevent over-pressurization of the bleb area.

In some examples, the pressure sensor P4 is disposed downstream of the pump to monitor the bleb pressure. Although several arrangements are contemplated, in this embodiment, the pressure measurements are weighted in the algorithms or calculation performed by the processor so that the IOP will be decreased if necessary, at the expense of the bleb pressure.

The secondary control valve 512 serves multiple purposes. One of the purposes includes providing a redundant flow restrictor in the event of failure of the main control valve. Accordingly, even if the main control valve 510 were to fail, catastrophic eye depressurization will not occur. Another purpose of the secondary control valve 512 includes cooperative or independent control of the fluid flow. In some embodiments, the secondary control valve 512 can provide additional control functionality that may include, for example, using the main control valve 510 for coarse flow adjustments, such as on-off, and using the secondary control valve 512 for fine adjustments to flow, such as regulating the flow range with more preciseness than the main control valve.

The example shown in FIG. 5 includes the pump 514 connected in series adjacent the secondary control valve 512. In this example, the pump 514 is a bubble-driven pump arranged to increase the flow through the valve system 230. In this example, the pump 514 includes a housing 570, an entrance port 572, an exit port 574, and a pump control system 576. The entrance port 572 is in fluid communication with the exit port 520a of the secondary control valve 512. Although shown as being connected by a tube 568, some embodiments do not have a tube, but instead the secondary control valve 512 and the pump 514 are disposed so that the fluid flows directly from one port to another, and in some embodiments, the valves and the pump may share the same housing. In other embodiments, the pump is not present in the valve system, and the exit port 520a of the secondary control valve exits to the drainage site or a channel or a tube to the drainage site, which may include a bleb.

In the example shown, the pump 514 includes a one-way check valve 592 adjacent to the exit port 574. Here, the check valve 592 is disclosed as a deformable cantilever that prevents backflow. Other types of check valves are contemplated. For example, and without limitation, the check valve 592 may also be of the form of a spider valve with straight or bent arms, or a hybrid between a cantilever and a spider valve, or another form of check valve that is known in the art. This ensures that drainage fluid at the bleb does not reenter the valve system 230. In some embodiments, the check valve 592 will be disposed adjacent the exit port 520a of the secondary control valve 512.

As indicated in FIG. 5, the pump 514 may include a tapered opening into the pump at the entrance port 572 and the exit port 574 may include a narrow opening that increases in cross-sectional area. Accordingly, because of the shape of the openings, fluid flow will tend to flow easier out the exit port than out the entrance port. Some embodiments may include a one-way check valve such as those described above, in the line between the secondary control valve 512 and the pump 514, thereby eliminating the chance of fluid flow back toward the interior chamber of the eye.

The pump control system 576 includes, in a manner not unlike the valves 510, 512, a flow control chamber 580, actuator fluid 582, electrodes 584, a diffusion barrier 586, and a flexible membrane 588 (similar in form and function to 538). For a detailed description, please refer to the discussion above. The electrodes 584 are in communication with and controlled by the processor 215 in FIG. 2 and are controlled to increase fluid flow through the valve system.

Figure 6:
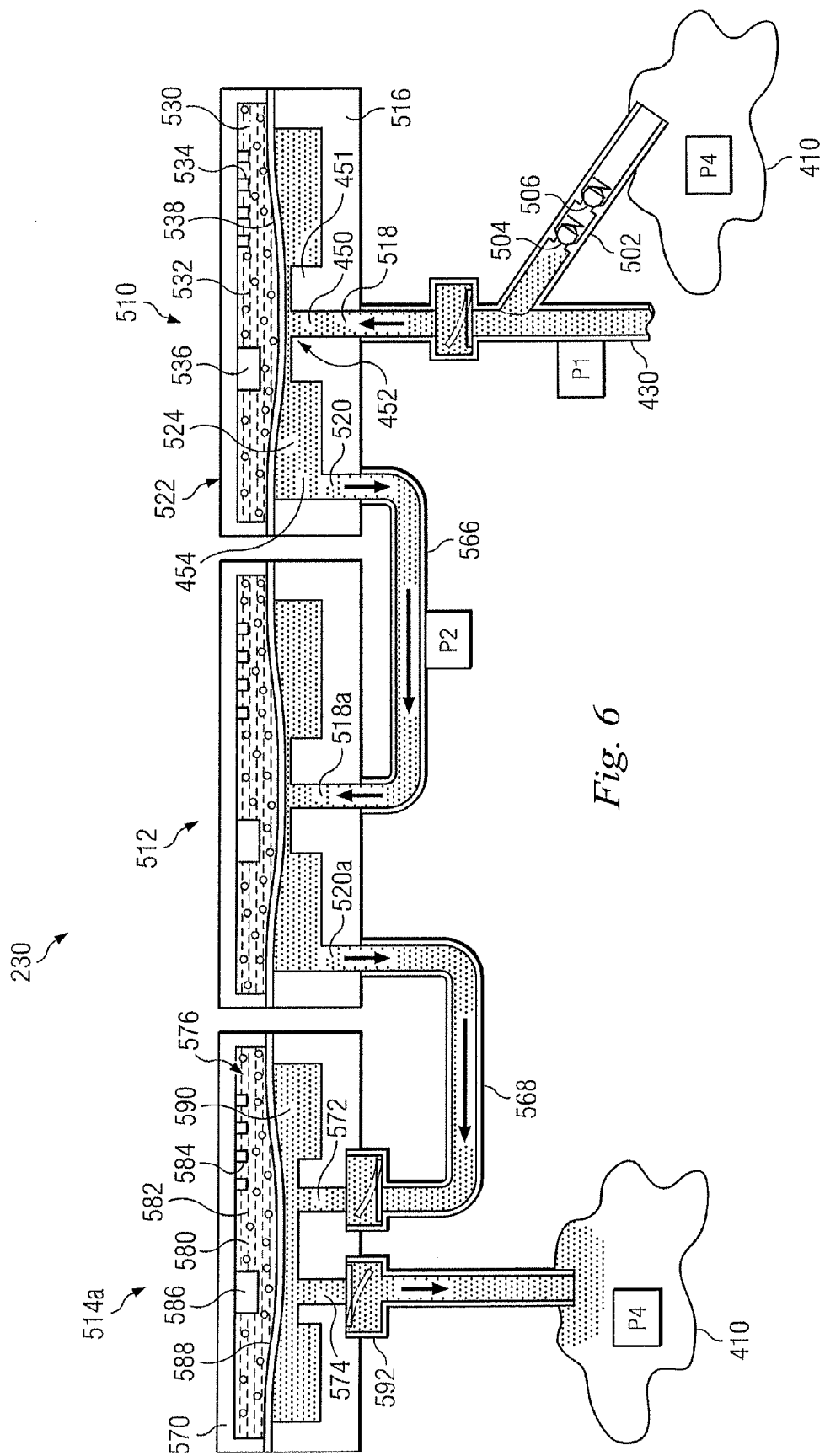
FIG. 6 is an illustration of a cross-sectional view of another exemplary valve system according to one embodiment consistent with the principles of the present disclosure, with a check valve between a pump and a valve.

The check valve 592 may assist with the pumping since downward deflection of the membrane 588 forces fluid through the check valve 592 toward the drainage site 410, yet when the pressure reduces, the movement of the membrane 588 pulls fluid from the tube 568 and the valve system, and not from the drainage site 410. FIG. 6 shows another embodiment of the pump 514a, with a second check valve disposed along the tube 568.

It is worth noting that for biocompatibility, the devices disclosed herein may be coated or encapsulated in a material such as polypropylene, silicone, parylene, or other materials.

In operation, the electrodes 584 generate bubbles in the actuator fluid 582 through electrolysis, increasing the volume of solution in the flow control chamber 580. To accommodate the increase in volume, the flexible membrane 588 expands into an interior chamber 590 of the pump 514, displacing the drainage fluid to force fluid out of the exit port 574. Accordingly, the pump 514 may be actuated a plurality of times to force the drainage fluid through the pump into the drainage site.

The pump 514 is configured to create pressure surges to clear any tube occlusions in the system, including the drainage tube 430. Further, in the event that pressure is required in the bleb for drainage, the pump can provide additional pressure to drive fluid and lower IOP. For example, the pump 514 can reduce IOP by creating additional work for overcoming resistance due to fibrosis in the orbit (eye socket)/subconjunctival drainage site 410.

In one example and as shown in FIG. 5, the drainage tube 430 is bifurcated to provide an override pressure relief line 502 that includes an override pressure relief valve 504 at the drainage site 410. The pressure relief valve may be a pressure driven membrane type valve/check valve such as a flapper valve having a fixed threshold spring rate that opens when pressure exceeds the threshold spring rate. In one exemplary embodiment, the pressure relief valve includes a second backup valve 506 that adds redundancy to the override pressure relief system. Note that relief line 502 may be routed in such a way that it branches off from the substrate base allowing the incorporation of those check valves defined above to be incorporated into the fabrication of the entire system.

The processor 215 may be configured to balance the IOP with the bleb pressure to maintain the IOP pressure at acceptable levels, while at the same time accounting for the pressure in the bleb in order to reduce fibrosis and increase or regulate the capacity of the bleb to absorb fluid without undue expansion or pressure.

In use, the IOP control system 200 is implanted in an eye in a conventional manner. The pressure sensors are disposed about the control system 200 in the manner described above. Particularly, the sensor P1 is disposed and configured to measure pressure in the interior eye, sensor P2 is disposed and configured to measure pressure within the valve system, sensor P3 is disposed and configured to measure atmospheric pressure, and sensor P4 is disposed and configured to measure Bleb pressure.

The IOP control system is configured to adjust the flow through the valve system 230 based on measured pressure values or derivatives from the pressure sensors. If the pressures are not within desired ranges, the TOP control system 200 may adjust the valve system 230 to increase or decrease drainage flow through the drainage tube 430 to effect a pressure change to the desired pressure. To do this, the processor 215 operates the valve system 230 with the power source 205 to activate or deactivate the electrodes in the main control valve 510, the secondary control valve 512, and/or the pump 514. The electrodes act within the actuator fluid to change at least a portion of the liquid to a gaseous state, increasing the pressure within the flow control chamber. Over time these molecules recombine to change into a liquid state, decreasing the pressure and likewise the volume. To slow the state change, the diffusion barrier increases the diffusion length moieties need to travel to recombine, and also may capture and/or slow gaseous molecules within its passageways.

As the liquid state partially changes to a gas state, the increasing pressure in the flow control chamber acts against the flexible membrane to displace it and increase the overall volume of the chamber. In so doing, the membrane moves into the passageway, obstructing the flow path. In some instances, if desired, the flexible membrane may cover the entire first portion of the passageway, and may further engage against and cover the entire upper surface of the boss 451.

The drainage fluid, so long as it is flowing, is then directed from the first control valve 510 to the second control valve 512. The second control valve 512 may provide redundancy in some aspects, or may provide an additional level of control in other aspects. Accordingly, the processor may operate the electrodes in a manner to achieve the desired pressures as indicated above.

In embodiments employing the pump 514, the processor 215 may control the pump electrodes 584 to provide additional pumping when, for example, the bleb pressure is about equivalent to the inner chamber pressure, and the IOP is outside an acceptable pressure range. The pump operation includes generating bubbles at the pump to displace the flexible membrane as discussed above. Repeated displacement of the flexible membrane 588 drives fluid flow through the pump.

Figure 7:
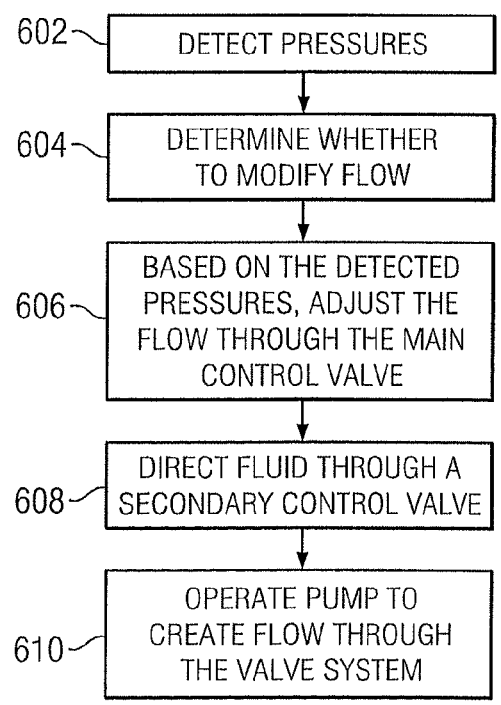
FIG. 7 is a flow chart of an exemplary method of operating an IOP control system in accordance with one embodiment of the present disclosure.

FIG. 7 shows an exemplary method of operating an IOP control system in accordance with one embodiment of the present disclosure. The method begins with the sensors P1-P4 detecting pressures at a step 602 and the processor 215 receiving the data from the sensors.

At a step 604, based upon algorithms, programs, or coding in the processor or memory, the processor 215 determines whether any flow modifications are required to maintain the IOP or the anterior chamber pressure within a desired target range and whether any modification is required to maintain the bleb pressure within a target range. In some aspects, the processor 215 compares measured pressure data to stored pressure data and determines whether the data is inside or outside acceptable ranges.

For example, in some aspects, determining whether flow modifications are required may include comparing the anterior chamber pressure as measured by sensor P1 to the atmospheric pressure as measured by sensor P3, and determining whether the main control valve 510 should be modified based on the comparison. It may also include comparing the outlet pressure from the main control valve 510 as detected by sensor P2 to the bleb pressure at the drainage site as detected by pressure sensor P4 and/or atmospheric pressure detected by sensor P3, and determining whether the secondary control valve 512 should be modified based on the comparison to prevent over-pressurization of the bleb area. Other examples include other pressure relationships as determined by algorithms to control one or both of the control valves 510, 512. In some embodiments, the fluid is routed to the optional pump 514 to allow the valve system 230 to deliberately create an overpressure when needed to clear a bleb or other obstruction.

In some examples, the pressure sensor P4 is disposed downstream of the pump 514 to monitor the bleb pressure. Although several arrangements are contemplated, in one embodiment, the pressure measurements are weighted in the algorithms or calculation performed by the processor so that the IOP will be decreased if necessary, at the expense of the bleb pressure. Also, taking into account the pressure at the drainage site, the processor 215 in FIG. 2 may control the secondary control valve 512 to control flow that ensures the bleb size is minimized and the bleb pressure is properly controlled.

If the system determines flow modifications are needed at step 604, the processor signals the appropriate electrodes in the main control valve 510, the secondary control valve 512, and/or the pump 514 at step 606. In the examples disclosed herein, the control valves and the pump are bubble operated devices that modify flow paths using pressure changes in the membranes resulting from phase changes occurring during electrolysis procedures as discussed above.

During this process, at least a portion of the gas interacts with the diffusion barrier to prolong the state change back to liquid resulting in decreased pressure in the valve flow control systems. Further, due to the state changes, the flexible membrane that forms a part of the passageway flexes to increase or decrease the cross-sectional area of the passageway to affect flow resistance, and ultimately control flow.

At a step 608, the drainage fluid is directed to the secondary control valve 512. The secondary control valve 512 may be controlled in any of a number of ways consistent with the control of the main control valve 510. In some examples, the processor controls the secondary control valve based on data measured by the sensors P4 and P3. In other examples, the processor controls the secondary control valve based on additional data measured by including the sensors P1 and P2. By taking into account pressure at the drainage site, such as the bleb pressure, the system can achieve control not previously attained.

In one example, the secondary control valve 512 has finer resolution in regards to controllability than the main control valve 510. With the valves arranged in this manner, the valve system may achieve a more accurate variety of possible set points. For example, gross adjustments may be accomplished by adjusting the main control valve 510 while fine adjustments may be accomplished by adjusting the secondary control valve 512.

In addition, the use of primary and secondary control valves provide a more accurate control to a user because they enable the valve system 230 to have an increased variety of possible set points. That is, for any single set point acquired with the primary control valve, the secondary control valve provides a whole range of additional control.

In some examples, at a step 610, the processor 215 operates the pump 514 to increase flow through the valve system 230. Such additional flow may become important when, for example, bleb pressure equals the anterior chamber pressure or when obstructions may be disposed in the flow lines of the IOP control system.

As described above, the override pressure relief valve may come into play when IOP increases above preset values and the valve system is not as responsive as desired.

In some examples, the processor controls the IOP control system 200 to provide pumping or valve control only at certain times or when preset criteria are met. In one example, the pump is activated to pump aqueous from an anterior chamber of the eye while the patient sleeps. The pump may be deactivated while the patient is awake. In another example, the processor receives and processes information from the sensor system 210 only at preset increments of time. In one example, the increment is greater than thirty seconds and less than one hour. In response to this incremental consideration of the measured pressure, the processor may direct power from the power source to the active valve. Based on these measurements, the processor may also direct further adjustment of the active valve to change the intraocular pressure of an eye.

The systems and methods described herein achieve IOP control with very low power and with a very small device. The bubble-driven system accomplishes this using electrolysis to affect drainage flow. The system also takes into account bleb pressure in regulating drainage flow. Accordingly, based on pressure sensor inputs and periodic power boosts to control the flow-regulating control valves, the system provides suitable eye care for a patient. In some examples, sufficient power is provided through on-board batteries or unobtrusive wireless (external) powering.

Conventional passive check valves in drainage device implants (e.g. Ahmed Valve) only support reduced risk of hypotony in the weeks immediately following surgery. But these conventional valves have no mechanism for controlling bleb pressure. The system disclosed herein can control bleb pressure and may also include an active pump for creating pressure surges to clear any tube occlusions. Further, in the event that pressure is required in the bleb for drainage, the optional pump can provide additional pressure to drive fluid and lower IOP.

Accordingly, the systems and methods disclosed herein provide a device that a) requires minimal power (internal or external), b) based on the theory of operation that little or no bleb pressure is required for drainage, the system disclosed herein presents a mechanism of minimizing bleb height (reducing or eliminating bleb), which could significantly reduce the effect of fibrosis and also reduce or eliminate other issues related to blebs and bleb management, and c) in the event pressure is required in the bleb for drainage, the pump can provide additional pressure to drive fluid and lower IOP.

Persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure

We claim:

1. An intraocular pressure ("IOP") control system for implantation in an eye of a patient to provide drainage from an anterior chamber of the eye to a drainage site at the eye, comprising:
    a drainage tube with a first end configured to be located in the anterior chamber and a second end, the drainage tube being configured to convey fluid from the anterior chamber toward the drainage site to relieve intraocular pressure;
    a valve system in fluid communication with the drainage tube and configured for implantation in the eye, the valve system being arranged to control drainage flow through the drainage tube between the anterior chamber and the drainage site, the valve system being configured to control fluid flow using an electrolysis system; and
    an override pressure relief system comprising:
        an override pressure relief line with a first end fluidly coupled to the drainage tube and a second end configured to be located at the drainage site; and
        an override pressure relief valve coupled to the override pressure relief line, the override pressure relief valve configured to operate when intraocular pressure increases above preset values and the valve system is not sufficiently responsive.

2. The IOP control system of claim 1, wherein the valve system comprises an actuator liquid and the electrolysis system is configured to generate bubbles by converting at least a portion of the actuator liquid to a gas.

3. The IOP control system of claim 2, wherein the electrolysis system comprises a pair of electrodes.

4. The IOP control system of claim 3, wherein the pair of electrodes are interdigitated.

5. The IOP control system of claim 2, wherein the valve system comprises a diffusion barrier disposed adjacent the actuator liquid, the diffusion barrier being sized to reduce the rate of state change from gas molecules to liquid molecules.

6. The IOP control system of claim 1, wherein the valve system comprises an aqueous flow passageway and a flexible membrane forming a part of the passageway, the flexible membrane being configured to flex as a result of an electrolysis process.

7. The IOP control system of claim 6, wherein the flexible membrane is configured to displace and modify the cross-sectional area of the passageway.

8. The IOP control system of claim 6, wherein the passageway includes a first portion having a flow path substantially perpendicular to the flexible membrane.

9. The IOP control system of claim 6, wherein the passageway comprises a first portion directed substantially at a central portion of the flexible membrane, such that flexure of the flexible membrane affects the flow rate of fluid through the first portion.

10. The IOP control system of claim 6, wherein the flexible membrane has corrugations, to increase the flexibility of the flexible membrane.

11. The IOP control system of claim 1, wherein the valve system comprises a first valve and a second valve connected in series, each of the first and second valves being configured to control flow using an electrolysis process.

12. The IOP control system of claim 1, further comprising a pump.

13. The IOP control system of claim 12, wherein the pump comprises an electrolysis system.

14. The IOP control system of claim 1, further comprising a sensor system comprising:
    a first sensor configured to detected pressure in the anterior chamber;
    a second sensor configured to detect atmospheric pressure; and
    a third sensor configured to detect pressure at the drainage site.

15. The IOP control system of claim 14, further comprising a processor configured to receive data from the first, second, and third sensors and send control signals to the valve system based on the data.

16. The IOP control system of claim 15, further comprising a power source coupled to the processor and the valve system.

17. The IOP control system of claim 16, further comprising a radio frequency antenna coupled to the power source and the processor for recharging, programming and data transfer.

18. The IOP control system of claim 14, further comprising a first barrier separating the first and second sensor and a second barrier separating the second and third sensor, and a third barrier separating the first and third sensors.

19. The IOP control system of claim 18, wherein the third barrier separating the first sensor and the third sensor is the valve system.

20. The IOP control system of claim 14, wherein the second sensor is configured to be disposed under a conjuctiva of the eye.

21. The IOP control system of claim 14, wherein the valve system comprises a plate having a barrier thereon, and the second sensor is disposed on a top of the plate and the third sensor is disposed on a bottom in contact with the drainage site.

22. An intraocular pressure ("IOP") control system for implantation in an eye of a patient to provide drainage from an anterior chamber of the eye to a drainage site at the eye, comprising:
 a drainage tube with a first end configured to be located in the anterior chamber, the drainage tube being configured to convey fluid from the anterior chamber;
 a first sensor configured to detect pressure in the anterior chamber;
 a second sensor configured to detect atmospheric pressure;
 a third sensor configured to detect pressure at the drainage site;
 a valve system in fluid communication with the drainage tube and configured for implantation in the eye, the valve system being arranged to control drainage flow through the drainage tube between the anterior chamber and the drainage site;
 a processor in communication with and configured to receive data from the first, second, and third sensors, the processor being configured to control the valve system based on the received data to maintain desired pressures in the anterior chamber and at the drainage site; and
 an override pressure relief system comprising:
  an override pressure relief line with a first end fluidly coupled to the drainage tube and a second end configured to be located at the drainage site; and
  an override pressure relief valve coupled to the override pressure relief line, the override pressure relief valve configured to operate when intraocular pressure increases above preset values and the valve system is not sufficiently responsive.

23. The IOP control system of claim 22, wherein the valve system is configured to control drainage fluid flow using an electrolysis process.

24. The IOP control system of claim 22, wherein a radio frequency antenna coupled to an onboard power source and processor for recharging, programming and data transfer.

25. The IOP control system of claim 22, further comprising a first barrier separating the first and second sensor and a second barrier separating the second and third sensor, and a third barrier separating the first and third sensors.

26. The IOP control system of claim 25, wherein the third barrier separating the first sensor and the third sensor is the valve system.

27. The IOP control system of claim 22, wherein the second sensor is configured to be disposed under a conjuctiva of the eye.

28. The IOP control system of claim 22, wherein the valve system comprises a plate having a barrier thereon, and the second sensor is disposed on a top of the plate and the third sensor is disposed on a bottom in contact with the drainage site.

* * * * *